United States Patent [19]

Peeters et al.

[11] Patent Number: 5,674,500
[45] Date of Patent: *Oct. 7, 1997

[54] VACCINES AGAINST AUJESZKY'S DISEASE AND OTHER ANIMAL DISEASES CONTAINING PSEUDORABIES VIRUS MUTANTS

[75] Inventors: Bernardus Petrus Hubertus Peeters; Jan Marie Antonius Pol; Arnold Leonard Josef Gielkens, all of Lelystad; Robertus Jacobus Maria Moormann, Dronten, all of Netherlands

[73] Assignee: Akzo Nobel N.V., Arnhem, Netherlands

[*] Notice: The term of this patent shall not extend beyond the expiration date of Pat. No. 5,626,850.

[21] Appl. No.: 373,325

[22] PCT Filed: Jul. 8, 1993

[86] PCT No.: PCT/NL93/00146

§ 371 Date: Jan. 9, 1995

§ 102(e) Date: Jan. 9, 1995

[87] PCT Pub. No.: WO94/01573

PCT Pub. Date: Jan. 20, 1994

[30] Foreign Application Priority Data

Jul. 9, 1992 [EP] European Pat. Off. ............ 92202096

[51] Int. Cl.$^6$ .................. A61K 39/245; A61K 39/295; C12N 7/01
[52] U.S. Cl. .................. 424/199.1; 424/229.1; 435/235.1; 435/320.1; 935/65
[58] Field of Search ............ 435/235.1, 236, 435/172.3, 320.1; 424/229.1, 205.1, 199.1; 935/65

[56] References Cited

U.S. PATENT DOCUMENTS 4,999,296  3/1991  Kit et al. ............... 435/235.1
5,352,575  10/1994  Petrovskis et al. ......... 435/5

FOREIGN PATENT DOCUMENTS

WOA 9 102 795  3/1991  WIPO.
WO92/05263  4/1992  WIPO.
94/03595  2/1994  WIPO .................. A61K 39/245

OTHER PUBLICATIONS

N. de Wind et al., *Journal of Virology,* 64:10:4691–4696, Oct. 1990.
I. Rauh et al., *Journal of Virology,* 65:10:5348–5356, Oct. 1991.
B. Peeters et al., *Journal of Virology,* 66:2:894–905, Feb. 1992.
C.C. Marchioli et al., *Journal of Virology,* 61:12:3977–3982, Dec. 1987.
D.C. Johnson et al., *Journal of Virology,* 62:12:4605–4612, Dec. 1988.
S. Heffner et al., *Journal of Virology,* 67:3:1529–1537, Mar. 1993.
H. Ishii et al., *J. Gen. Virol.,* 69:1411–1414 (1988).
M.D. McFarland et al., *Can J Vet Res,* 51:3:340–344, 1987.
P. Vannier, DVM, *Am J Vet Res,* 46:7:1498–1502, Jul. 1985.
W.L. Mengeling et al., *Am J Vet Res,* 53:11:2164–2173, Nov. 1992.
C. Marcholi et al., *Am. J. Vet Res,* 49:6:860–864, Jun. 1988.
J.T. van Oirschot et al., *Agriculture,* Seminar, pp. 281–290, Belgium, Dec. 1984.
A.O. Fuller et al., *Journal of Virology,* 63:8:3435–3442, Aug. 1989.
U.A. Gompels et al., *Journal of Virology,* 63:11:4744–4755, Nov. 1989.
C.C. Marcholi et al., *Am J Vet Res,* 48:11:1577–1583, Nov. 1987.
T.C. Mettenleiter et al., *Journal of General Virology,* 75:1723–1733, 1994.
T.C. Mettenleiter et al., *Comp Immun Microbiol Infect Dis,* 14:2:151–16, 1991.
T. Kimman et al., "Contribution of single genes within the unique short region of Aujesky's disease virus (suid herpesvirus type 1) to virulence pathogensis and immunogenicity," *Journal of General Virology* 73:PT2:243–251, Feb. 1992, UK.
B. Peeters et al., "Envelope glycoprotein gp50 of pseudorabies virus is essential for virus entry but is not required for viral spread in mice," *Journal of Virology,* 67:1:170–177, Jan. 1993, USA.

Primary Examiner—Mary E. Mosher
Attorney, Agent, or Firm—Mary E. Gormley

[57] ABSTRACT

The invention provides vaccines for preventing and controlling animal diseases, comprising a pseudorabies virus containing glycoprotein gp50 and having a mutation in its gp50 gene. The vaccines are suitable for use against Aujeszky's disease (pseudorabies), or against other animal diseases when the mutation is an insertion comprising a heterologous gene encoding an antigen corresponding to said animal disease. The pseudorabies virus may additionally have at least one mutation in one of its other genes, such as the gp63 gene or the gI gene. The vaccines are unable to spread from vaccinated to non-vaccinated animals.

10 Claims, 2 Drawing Sheets

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: other nucleic acid
        ( A ) DESCRIPTION: /desc = "synthetic"

( i i i ) HYPOTHETICAL: NO

( i v ) ANTI-SENSE: NO

( x i ) SEQUENCE DESCRIPTION: SEQ ID NO: 1:

TAGGCTAGAA TTCTAGCCTA      20

( 2 ) INFORMATION FOR SEQ ID NO: 2:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear     ( i i ) MOLECULE TYPE: other nucleic acid
        ( A ) DESCRIPTION: /desc = "synthetic"

( i i i ) HYPOTHETICAL: NO

( i v ) ANTI-SENSE: NO

( x i ) SEQUENCE DESCRIPTION: SEQ ID NO: 2:

AATTCTAGCC TA      12

( 2 ) INFORMATION FOR SEQ ID NO: 3:

```
( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic"

( i i i ) HYPOTHETICAL: NO ( i v ) ANTI-SENSE: NO ( x i ) SEQUENCE DESCRIPTION: SEQ ID NO: 3:
```

AGGTTCCCAT ACACTAGTCC GCCAGCGCCA TGC                33

```
( 2 ) INFORMATION FOR SEQ ID NO: 4:

( i ) SEQUENCE CHARACTERISTICS:
            ( A ) LENGTH: 32 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "synthetic"

( i i i ) HYPOTHETICAL: NO ( x i ) SEQUENCE DESCRIPTION: SEQ ID NO: 4:
```

CCCGGTCCGT AGCCTAGGCA GTACGGCGT CG                  32

```
( 2 ) INFORMATION FOR SEQ ID NO: 5:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "synthetic"

( i i i ) HYPOTHETICAL: NO ( i v ) ANTI-SENSE: NO ( x i ) SEQUENCE DESCRIPTION: SEQ ID NO: 5:
```

CTAGTGAATT CGATATCAAG CTTC                          24

```
( 2 ) INFORMATION FOR SEQ ID NO: 6:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc = "synthetic"

( i i i ) HYPOTHETICAL: NO ( x i ) SEQUENCE DESCRIPTION: SEQ ID NO: 6:
```

CTAGGAAGCT TGATATCGAA TTCA                          24

VACCINES AGAINST AUJESZKY'S DISEASE AND OTHER ANIMAL DISEASES CONTAINING PSEUDORABIES VIRUS MUTANTS

BACKGROUND OF THE INVENTION

The invention relates to conditional lethal mutants of pseudorabies virus (PRV), also called Aujeszky's disease virus (ADV). PRV is a highly neurotropic herpesvirus that causes Aujeszky's disease in domestic and wild animals (for reviews see Mettenleiter, Comp. Immun. Microbiol. Infect. Dis. 14, 151–163 [1991]; Wittmann and Rziha, in [G. Wittmann ed.] Herpesvirus Diseases of Cattle, Horses and Pigs, Kluwer, Boston, 230–325 [1989]; Pensaert and Kluge, in [M. B. Pensaert ed.] Virus infections of porcines, Elsevier Science Publishers B.V., Amsterdam, 39–64 [1989]). Pigs are relatively resistant against PRV and therefore are considered the natural host of the virus. The natural portal of entry is the nasopharyngeal region. The virus is able to replicate in cells of the nasal and pharyngeal mucosa, and after infection of peripheral nerves it is transported to the central nervous system where it causes severe encephalitis which is often fatal in young pigs. Older pigs usually survive the infection, but may develop fever and pneumonia. Infection of sensory ganglia generally results in the establishment of latency.

Vaccination against Aujeszky's disease is carried out to limit the economic damage caused by mortality and growth retardation in infected animals. For this purpose, vaccines based on attenuated live virus and on inactivated virus are available. Attenuated live virus vaccines are generally preferred, since they are more easily produced and therefore less expensive than inactivated vaccines. Moreover, attenuated virus can be administered intranasally which provides better protection than parenteral vaccination with either attenuated live virus or inactivated virus.

Early vaccines based upon attenuated live virus strains obtained after serial passage in call culture possessed several disadvantages. Such vaccines were not homogenous and viral variants of unknown virulence and immunogenicity were included in the mixtures. Moreover, such vaccines suffered from a risk of reverting to virulence. More recently, the increased knowledge, at molecular level, of the structure and replication of viruses, and the availability of sophisticated molecular biological techniques, have enabled scientists to design attenuated vaccines rather than to rely upon chance. Vital genetics and DNA sequence analysis enable the identification of the regions in the viral genome where alterations can contribute to the attenuation of viral pathogenicity. Recombinant DNA technology allows such regions to be altered or deleted, leading to the production of an attenuated virus with defined and stable alterations. This approach was first applied successfully by Kit and coworkers (Am. J. Vet. Res. 46, 1359–1367 [1985]) for the attenuation of PRV. Inactivation of the thymidine-kinase (TK) gene of PRV resulted in a greatly reduced virulence for pigs (EP-A-141.458). In addition to the lesion in the TK gene, deletions have been introduced in glycoprotein genes such as gI, gIII and gX (Kit et al., Am. J. Vet. Res. 48, 780–793 [1987]; Marchioli et al., Am. J. Vet. Res. 48, 1577–1583 [1987]; Quint et al., J. Gen. Virol. 68, 523–534 [1987]; Moormann et al., J. Gen. Virol. 71, 1591–1595 [1990]; WO-A-9102795) leading to a further reduction in the virulence of the virus and to the ability to serologically distinguish vaccinated animals from infected animals (Platt et al., Vet. Microbiol. 11, 25–40 [1986]; Van Oirschot et al., J. Gen. Virol. 67, 1179–1182 [1986]; Van Oirschot et al., J. Virol. Meth. 22, 191–206 [1988]; Eloit et al., Vet. Rec. 128, 91–94 [1989]).

A new approach to vaccine development is the expression of genes of foreign pathogens using live attenuated viral vaccine strains as carrier (viral vaccine vectors). Expression of antigens by a live vector virus mimics expression after natural infection and may stimulate both humoral and cellular immune responses. Vaccine vectors may be used for immunization against diseases for which no adequate vaccines are currently available, or which cannot be safely or easily produced.

The development of vaccine vectors has focused mainly on vaccinia virus (Moss and Flexnet, Ann. Rev. Immunol. 5, 305–324 [1987]; Piccini and Paoletti, Adv. Virus Res. 34, 43–64 [1988]). Vaccinia virus has been used extensively for the eradication of smallpox in man and has been shown to be highly effective and relatively safe. The broad host range and the capacity to accomodate large amounts of foreign DNA has made vaccinia the virus of choice to be tested as vaccine vector (Hruby, Clin. Microbiol. Rev. 3, 153–170 [1990]; Tartaglia et al., Crit. Rev. Immunol. 10 13 [1990]). As an alternative to vaccinia virus, other poxviruses such as raccoonpox virus, avipox viruses, capripox virus and suipox virus are being developed as vaccine vectors (Tayor et al., Vaccine 6, 504–508 [1988]; Lodmell et al., J. Virol. 65, 3400–3405 [1991]; Letellier et al., Arch. Virol. 118, 43–56 [1991]).

Other viruses which can be used as vaccine vectors include adenoviruses (Berkner, BioTechniques 6, 6003–6020 [1988]) and herpesviruses (Shih et el., Proc. Natl. Aced. Sci. U.S.A. 81, 5867–5870 [1984]; Thomsen et el., Gene 57, 261–265 [1987]; Lowe et el., Proc. Natl. Aced. Sci. U.S.A. 84, 3896–3900 [1987]; Cole et el., J. Virol. 64, 4930–4938 [1990]; van Zijl et el., J. Virol. 65, 2761–2765 [1991]; Kit et el., Vaccine 9, 564–572 [1991]). The availability of safe and effective live herpesvirus vaccines in combination with the capacity to accomodate large amounts or foreign DNA makes these viruses attractive candidates for the development of vaccine vectors. The use of PRV as a vaccine vector is very promising. PRV has been well characterized, and safe and effective live vaccines have been developed by means of targeted deletions (see above). The virus has a broad host range but is harmless for humans. The application or PRV as an efficient carrier vaccine has recently been demonstrated by van Zijl et el. (J. Virol. 65, 2761–2765 [1991], WO-A-9100352), who showed that PRV recombinants that expressed envelope glycoprotein E1 of hog cholera virus protected pigs against both pseudorabies and hog cholera (classical swine fever).

One of the most important properties of vaccines is their safety. Because the exact molecular changes that have resulted in an altered phenotype of conventionally attenuated live vaccines are generally unknown, there is always a small chance that they will revert toward virulence. This problem can be eliminated by using recombinant vaccines that carry defined and stable deletions. However, the construction of stably attenuated vaccines is sometimes very difficult if not impossible. In that case one has to rely on killed vaccines or on the use of safe vaccine vectors. Properly prepared and tested, live attenuated deletion vaccines and vaccine vectors are generally safe in immunocompetent hosts. However, severe complications can occur in immunocompromised hosts. Since live attenuated vaccines and vaccine vectors are able to replicate, they can be released into the environment where they may pose a threat to immunocompromized hosts. Furthermore, a vaccine that is safe for use in the target species may still be virulent for other species.

Candidate genes for incorporation in vaccine vectors often code for structural virion proteins that are highly immunogenic. These proteins include viral glycoproteins, fusion proteins and haemagglutinin-neuraminidases (Hruby, Clin. Microbiol. Rev. 3, 153–170 [1990]). Such proteins are often involved in virus-cell interactions that determine the host- and/or cell-tropism of the virus. Therefore, expression of such genes by the carrier virus may theoretically alter its biological properties such as pathogenicity, tissue-tropism and host-specificity. Furthermore, these altered biological properties may be transferred, by means of homologous recombination, from the attenuated vector virus to a virulent wild-type virus.

The above-mentioned considerations argue for the development of live vaccines and vaccine vectors that are self-restricted, i.e., which are not disseminated by the vaccinee. Ideally, such a vaccine should produce non-infectious progeny and should be unable to generate infectious virus after recombination with the corresponding wild-type virus. Here we describe an invention that fulfills-these requirements.

SUMMARY OF THE INVENTION

The present invention provides conditional lethal pseudorabies virus (PRV) mutants that can be used for vaccination against Aujeszky's disease and which can be used as safe vaccine vectors. The strains of the invention are unable to express gp50, a virus envelope protein that is essential for infectivity of the virus. The gp50 gene has been inactivated, either by insertion of a foreign oligonucleotide, or by a deletion, or by both (substitution). In particular, the gp50 gene has been inactivated by the insertion of a synthetic oligonucleotide that contains translational stopcodons in all three reading frames, or by the deletion of a part of the PRV genome that comprises parts of both the gp50 gene and the gp63 gene. The mutant viruses are grown on a complementing cell line that expresses the viral gp50 gene. Progeny virions produced by these cells are pheno-typically complemented, i.e. they possess gp50 which is provided by the complementing cell line. Such phenotypically complemented mutant virions are able to infect cells both in vitro and in vivo, and are able to replicate and spread by direct cell-to-cell transmission. However, progeny virions released by the infected cells are non-infectious because they lack gp50. Since they cannot initiate a new infection cycle these viruses cannot be disseminated from the vaccinated animal to non-vaccinated animals. This restriction makes (carrier) vaccines based upon these viruses very safe.

Consequently, the invention relates to the use of pseudorabies virus gp50 mutants for preparing vaccines against animal diseases, either for preparing a vaccine against Aujeszky's disease or for preparing vector vaccines against other animal diseases by incorporating nucleotide sequences encoding antigens or part of antigens from other relevant pathogens into said mutants.

The invention further relates to vaccines for controlling an animal disease, comprising a pseudorabies virus containing glycoprotein gp50 and having a mutation in its gp50 gene. The vaccine may be intended for protection against Aujeszky's disease, wherein the mutation is a deletion, or for protection against other animal diseases, wherein the mutation is an insertion comprising a heterologous nucleotide sequence encoding an antigen or part of an antigen from another pathogen inducing said other animal disease. The pseudorabies virus may contain other mutations in its genome for modifying its virulence or for expressing other proteins, such as deletions and/or insertions in its gp63, gI, gIII, gX, 11K, thymidine kinase (TK), ribonucleotide reductase (RR) protein kinase or 28K gene, in particular its gI or gp63 gene.

DETAILED DESCRIPTION OF THE INVENTION

Figure 1:
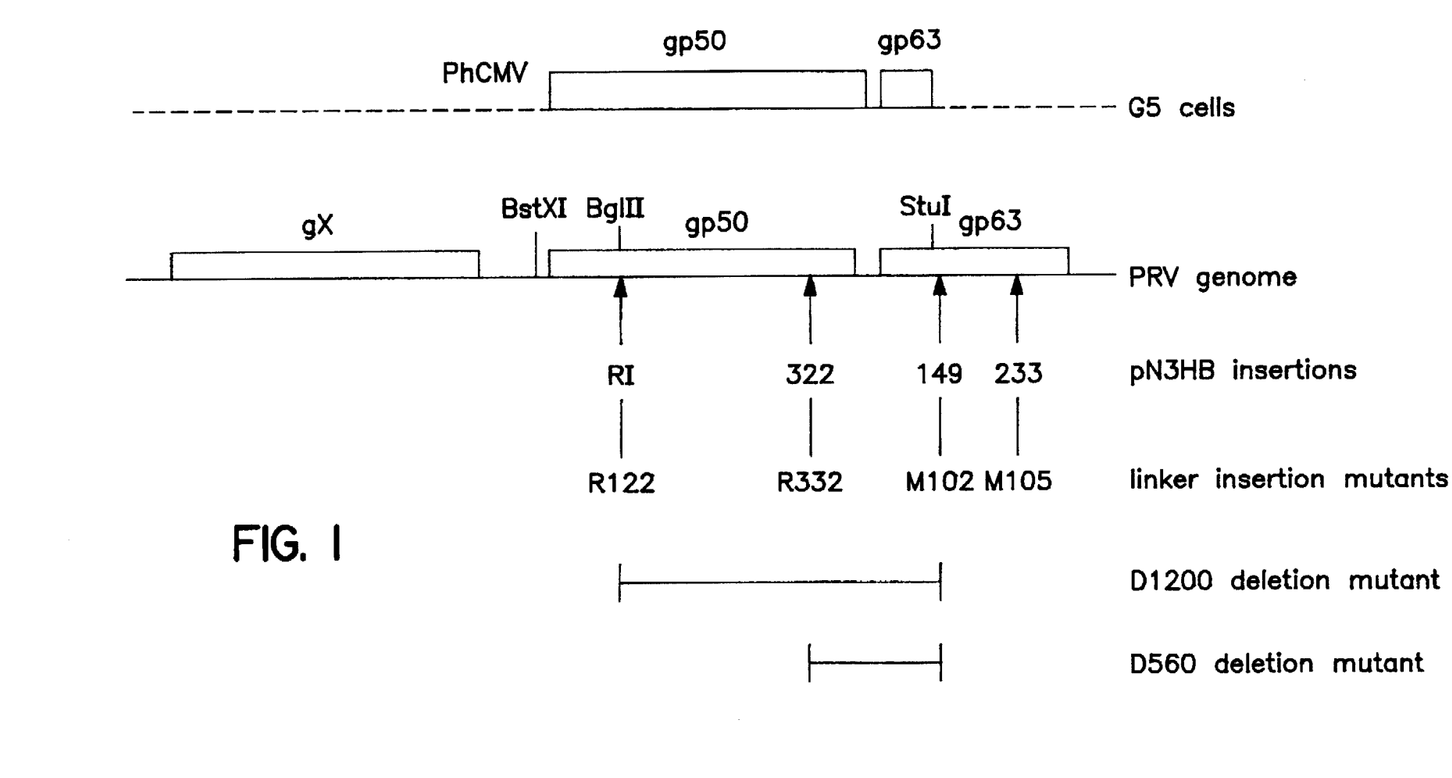

The invention relates to PRV gp50 mutants, exemplified by strains R122, R332, D560 and D1200 (see FIG. 1). Strains R122 and R332 are unable to express functional gp50, whereas strains D560 and D1200 are unable to express either functional gp50 or functional gp63. Since gp50 is essential for virus penetration, these mutants are grown on a complementing cell line that expresses gp50. Although all strains are able to complete a full replication cycle in non-complementing cells, progeny virions released from such cells are non-infectious because they lack gp50. The observation that gp50 mutants are able to produce plaques on noncomplementing cell lines indicates that the virus can be transmitted from infected to uninfected cells.

A synthetic oligonucleotide with the sequence 5'-TAGGCTAGAATT-CTAGCCTA-3' (SEQ ID No 1), which contains an EcoRI restriction site (GAATTC) and translational stopcodons in all three reading frames, was inserted at two different positions in the gp50 gene of plasmid pN3HB as described by de Wind et al. (J. Virol. 64, 4691–4696 [1990]) (see FIG. 1), in order to obtain PRV strains R122 and R332. Plasmid pN3HB consists of the HindIII-B fragment of PRV cloned in plasmid pBR322 (van Zijl et al., J. Virol. 65, 2761–2765 [1988]). The resulting plasmids in which the oligonucleotide was inserted between nucleotides 366–367, and 996–997 of the gp50 gene, were designated R1 and 322, respectively. We use the nucleotide sequence numbering of the gp50 sequence of PRV strain Rice (FIG. 2 of Petrovskis et al., J. Virol. 59, 216–223 [1986]). It should be noted, however, that the nucleotide sequence of the gp50 gene of PRV strain NIA-3 differs from the sequence of strain Rice at position 364 (G to A) resulting in the presence of a BglII restriction site in the gp50 gene of strain NIA-3.

Reconstitution of viral genomes was performed by means of overlap recombination (van Zijl et al., J. Virol. 65, 2761–2765 [1988]) using a combination of the mutagenized fragment (either R1 or 322) and the three overlapping subgenomic wild-type PRV fragments derived from cosmids c-179, c-27 and c-443, together comprising the entire viral genome. Overlap recombination was carried out in a complementing cell line (G5 cell line) that constitutively expressed gp50 (Peeters et al., J. Virol. 66, 894–905 [1992]). The resulting virus strains were designated R122 and R332, respectively.

To obtain strain D560, we used plasmid 322 (see above) and another derivative of plasmid pN3HB, designated 149 (de Wind et el., J. Virol. 64, 4691–4696 [1990]), in which the oligonucleotide was inserted in the gp63 gene between nucleotides 352–353 (numbering according to FIG. 5 of Petrovskis et al., J. Virol. 60, 185–193 [1986]) (see FIG. 1). By replacing the BglII-EcoRI fragment of plasmid 149 with the BglII-EcoRI fragment of plasmid 322, a new plasmid was generated in which the nucleotide sequence between positions 996 of the gp50 gene and 353 of the gp63 gene was replaced by the sequence of SEQ ID No 1 (i.e. the sequence of the mutagenic oligonucleotide). This plasmid was used together with the overlapping wild-type fragments for the regeneration of virus by means of overlap recombination in G5 cells. The resulting virus was designated D560.

To obtain strain D1200, plasmid 149 was digested with restriction enzymes BglII and EcoRI, and the resulting larger fragment was circularized by means of T4 DNA ligase after the ends had been treated with the Klenow fragment of *E. coli* DNA polymerase I. In the resulting plasmid, the nucleotide sequence between positions 336 of the gp50 gene and 353 of the gp63 gene was replaced by the sequence AAT-TCTAGCCTA (SEQ ID No 2; i.e. remnant of the mutagenic oligonucleotide). This plasmid was used together with together with the overlapping wild-type fragments for the regeneration of virus by means of overlap recombination in G5 cells. The resulting virus was designated D1200.

The gp50 mutants R122 and R332, and the gp50+gp63 routants D560 and D1200 are able to produce plaques on noncomplementing SK6 cells. Plaques produced on SK6 cells by strains R122 and R332 are similar in size to plaques produced by the wild type parent strain NIA-3. Plaques produced on SK6 cells by strains D560 and D1200 are smaller in size, indicating the involvement of gp63 in the replication cycle of PRV.

Although cell-to-cell transmission is independent of gp50, the gp50 mutant viruses were not expected to replicate to an appreciable extent in live animals. Virulence of viruses is generally the result of replication at the primary sites of infection followed by spread of progeny virions to other parts of the body and extensive multiplication through multiple rounds of infection. Since gp50 mutants are only able to replicate at the primary site of infection, we expected these mutants to be non virulent. Furthermore, it was doubtful whether these mutants were immunogenic since gp50 itself is highly immunogenic as evidenced by the finding that gp50 is able to induce a protective immune response in pigs (Marchioli et al., J. Virol. 61, 3977–3982 [1987]; Mukamoto et al., Vet. Microbiol. 29, 109–121 [1991]; Riviere et al., J. Virol. 66, 3424–3434 [1992]). Thus, inactivation of gp50 might severely reduce the immunogenic properties of the gp50 and gp50+gp63 mutants. Also, it was not expected that the mutant viruses would be able to reach the central nervous system, since this would involve transmission of the virus from infected tissue to peripheral nerves followed by transport to the central nervous system. If trans-synaptic transport of the virus involves reinfection of post-synaptic neurons by infectious progeny virions (Lycke et al., J. Gen. Virol. 65, [1984]; Card et al., J. Neurosci. 10, 1974–1994 [1990]), transport of the mutant virus to the central nervous system might be blocked at synapses. This would preclude the virus from entering the central nervous system, thus prohibiting its devastating effect in the brain.

To determine whether gp50 mutant viruses are able to spread in animal tissue, we studied replication of gp50 mutants R122 and R332, and gp50+gp63 mutants D560 and D1200 in explants of porcine nasal mucosa by means of immunohistochemistry. In addition, mice were infected subcutaneously or intraperitoneally to determine whether the viruses replicate and spread in vivo. Our results showed that all mutants are able to replicate in porcine nasal mucosa.

To our surprise, the gp50 mutants and gp50+gp63 mutants proved to be lethal for mice after intraperitoneal or subcutaneous inoculation. The virulence (expressed as mean time to death of infected animals) of strain R122 was only moderately reduced compared to the wild-type strain NIA-3. The virulence of strains D560 and D1200, however, was much more reduced, indicating the involvement of gp63 in virulence for mice. Post mortem examination of infected animals showed that the mutants were able to replicate in the brain. Immunohistochemical examination of organs of intraperitoneally infected animals showed that the virus preferentially replicated in peripheral nerves. When strain R122 was grown on non-complementing cells, and thus lacked gp50, infection by the intraperitoneal route was unsuccessful. This finding indicates that gp50 is required for the primary infection. The observation that a phenotypically complemented PRV gII mutant (which also produces non-infectious progeny but which is unable to produce plaques on noncomplementing cell lines) is completely harmless for mice indicates that, after primary infection, successful viral spread is dependent on cell-to-cell transmission. The finding that infectious virus could not be isolated from any of the animals that were infected with the gp50 or gp50+gp63 mutants, shows that progeny virions produced in live animals by these mutants are noninfectious.

Together, these results show that gp50 is required for the primary infection but not for subsequent replication and transmission of the virus, indicating that direct cell-to-cell transmission is a major mechanism of viral spread in vivo. These results furthermore indicate that trans-synaptic transport of the virus is independent of gp50 and does not result from de novo infection of post-synaptic neurons by extracellular virions. The finding that infectious virus could not be isolated from any of the animals that were infected with the gp50 or gp50+gp63 mutants, shows that progeny virions produced in live animals by gp50 mutants are noninfectious. Thus replication of these mutants is restricted to the infected/vaccinated animal. The use of a gp50 mutant as the basis of a vaccine against Aujeszky's disease or as a recombinant carrier virus for the expression of heterologous genes will generate a very safe vaccine that only replicates in the vaccinated animal and does not spread to other animals, including other species. Furthermore, if the heterologous gene is inserted at the location of the gp50 gene in the carrier virus, recombination with wild-type virus will always result in the generation of noninfectious recombinants.

Pigs vaccinated with the gp50 mutant R122 were completely protected against clinical signs of Aujeszky's disease after challenge inoculation with the virulent wild-type strain NIA-3. Pigs vaccinated with the gp50+gp63 mutants D560 and D1200 showed short periods of fever and growth retardation but did not show neurological signs after NIA-3 challenge inoculation. These results indicate that PRV mutants that are only able to spread by means of cell-to-cell transmission are still highly immunogenic. Furthermore, these results showed for the first time that expression of gp50, which is one of the most immunogenic PRV proteins (see above), is not required for efficient protection of pigs against Aujeszky's disease. This result was unexpected.

A vaccine according to the present invention for preventing or controlling pseudorabies virus (Aujeszky's disease) infections contains a PRV having gp50 in its virus envelope and having a defunctionalized gp50 gene as described above as an active ingredient. It further contains usual components such as a suitable carrier, optional stabilizers, adjuvants, solubilizers, emulsifiers etc. The administration of the vaccine can be done in various ways, such as intradermally, subcutaneously, intramuscularly, intravenously, or intranasally. Intranasal administration is preferred. The vaccine may also contain other immunogens related to other diseases, to produce a multivalent vaccine.

When the PRV gp50 mutant is used as a virus vector, it contains, in addition to a mutation in its gp50 gene, and preferably as an insertion in its gp50 gene, genetic information derived from other pathogens, including viruses such as hog cholera (swine fever) virus, parvovirus, transmissible gastro-enteritis virus, porcine epidemic abortion and respiratory syndrome (PEARS, or mystery swine disease MSD, PRRS or SIRS), porcine respiratory coronavirus (PRCV), porcine endemic diarrhoea virus and influenza virus, and bacteria, such as *Pasteurella multocida, Bordetella bronchiseptica, Actinobacillus pleuropneumoniae, Streptococcus suis, Treponema hyodysenteria, Escherichia coli* and *Leptospira*, and mycoplasmata, such as *M. hyopneumoniae* and *M. lyorhinis*. Methods for cloning nucleic acid sequences of pathogens into PRV subgenomic fragments and subsequently intregrating these in the genome of a PRV are generally known. An example is described by Van Zijl et al. J. Virol. 62, 2191-2195 [19883].

Whereas PRV gp50 mutants are still able to spread by cell-to-cell transmission, mutations in the homologous genes of herpes simplex virus type 1 (HSV-1) and bovine herpes virus type 1 (BHV-1) result in virus mutants that are unable to spread by cell-to-cell transmission (Ligas and Johnson, J. Virol. 62, 1486-1494 [1988]; Fehler et al., J. Virol. 66, 831-839 [1992]). This indicates that differences exist in the function of gp50 of PRV on the one hand, and gD of HSV-1 and gIV of BHV-1 on the other. Using recombinant DNA techniques it may be possible to modify HSV-1, BHV-1 and other herpesviruses in such a way that they are able to spread by cell-to-cell transmission without generating infectious progeny, in a manner similar to PRV gp50 mutants. This would generate a number of safe herpesvirus (carrier) vaccines that can be used for the eradication and control of many animal and human diseases.

DESCRIPTION OF THE FIGURES

FIG. 1

Physical map of part of the PRV genome. The arrows indicate the positions of the premature stopcodons, introduced by linker insertion mutagenesis, in the gp50 gene and gp63 gene of plasmid pN3HB and the corresponding virus mutants R122, R332, M102 and M105 (Peeters et al., J. Virol. 66, 894-905 [1992]; de Wind et al., J. Virol. 64, 4691-4696 [1990]). The horizontal bars show the positions and the extent of the deletions in mutants D560 and D1200. The upper line shows the BstXI-StuI fragment of PRV that is present in G5 cells that constitutively express gp50 (Peeters et al., J. Virol. 66, 894-905 [1992]).

FIG. 2

Plasmid pEVhis13HCVE1 containing the hog cholera virus E1 gene together with the human cytomegalovirus enhancer/promoter, which plasmid is used for the construction of a PRV gp50 mutant containing a heterologous gene (see Example 6).

FIG. 3

Plasmid pBP53E1 containing the hog cholera virus E1 gene together with the human cytomegalovirus enhancer/promoter, within a part of the PRV genome at the site of the deleted gp50 gene, which plasmid is used for the construction of a PRV gp50 mutant containing a heterologous gene (see Example 6).

EXAMPLE 1

Cloning of the gp50 gene of PRV strain NIA-3 and construction of cell lines that express gp50.

All recombinant DNA methods were performed by standard techniques (Maniatis et al., Molecular cloning: a laboratory manual. Cold Spring Harbor Laboratory Press, Cold Spring Harbor, N.Y. [1982]). Plasmid pEVhis14 was derived from pSV2his (Hartman & Mulligan, Proc. Natl. Acad. Sci. USA 85, 8047-8051 [1988]) by replacing the EcoRI-BamHI fragment by a fragment containing the immediate early enhancer/promoter of human cytomegalovirus (hCMV) (Bernard et al., EMBO J. 6, 133-138 [1987]), followed by a synthetic oligonucleotide containing stopcodons in all three reading frames and a poly-adenylation site. Plasmid pEVhis10 was derived from pEVhis14 by deleting a BanuHI fragment that contains the hCMV enhancer/promoter. The gp50 gene of PBV was cloned as a BstXI-StuI fragment (lacking the gp50 promoter) into the EcoRV site located down-stream of the hCMV promoter in pEVhis14, yielding plasmid pEVhis14gp50. The construction and characterization of cosmids c179, c27 and c443, which contain overlapping subgenomic PRV fragments, and plasmid pN3HB, which contains the HindIII-B fragment or PRV in the HindIII site of a pBR322 derivative, has been described (van Zijl et al., J. Virol. 65, 2761-2765 [1988]). Inactivation of gp50-expression by means of linker-insertion at two different positions in the gp50 gene of pN3HB (insertions R1 and 322) has been described (de Wind et al., J. Virol. 64, 4691-4696 [1990]).

SK-6 cells were transfected with plasmid pEVhis14gp50 by means of electroporation. SK-6 cells were harvested by trypsinization, washed once in phosphate-buffered saline (PBS) at room temperature and resuspended at $2 \times 10^7$ cells/ml in ice-cold PBS. Ten µg of plasmid pEVhis14gp50 was added to 0.5 ml of cells which were kept at 0° C. in a sterile disposable electroporation cuvette (0.4 cm inner electrode distance; BioRad Laboratories), and a discharge of 1000 V was delivered at a capacitance setting of 25 µF using a BioRad GenePulser. The cells were left at 0° C. for 15 minutes, transferred to a 75 cm² flask containing 50 ml of medium and incubated overnight. Subsequently, transfected cells were trypsinized and replated at several dilutions in 100 mm petri dishes in medium containing 2.5 mM histidinol. Medium was changed every 3-4 days until colonies were clearly visible (7-10 days). Individual colonies were picked and grown in microtitre culture plates. Expression of gp50 was determined by an immunoperoxidase monolayer assay and by radioimmunoprecipitation using monoclonal antibody G50N2, and a cell line that expressed large amounts of gp50, as determined by radioimmunoprecipitation, was designated G5 (Peeters et al., J. Virol. 66, 894-905 [1992]).

EXAMPLE 2

Construction of Mutant Viruses

Mutant viruses R122 and R332 were constructed by means of overlap recombination in G5 cells, by using 3 cosmids (c-179, c-27 and described by van Zijl et al., J. Virol. 65, 2761-2765 [1988]) containing overlapping wild-type PRV sequences, and the HindIII-B fragments of the pN3HB derivatives RI or 322 (de Wind et al., J. Virol. 64, 4691-4696 [1990]) containing the mutagenic oligonucleotide 5'-TAGGCTAGAATTCTAGCCTA3' (SEQ ID No 1) between nucleotide positions 366-367, and 996-997 in the gp50 gene, respectively (FIG. 1). The viral DNA fragments were released from the plasmids by EcoRI digestion (cosmids) or HindIII digestion (clones R1 and 322) and were not further separated from vector sequences. Transfection was performed by means of electroporation (see above) using the BioRad Gene-Pulser and Capacitance Extender at settings of 250 V and 960 uF respectively. Cells were seeded in 6-well plates and after incubation for 3 h at 37° C. the medium was replaced by Earle's minimal essential medium containing 2% foetal calf serum, 1% methylcellulose and incubated at 37° C. until plaques appeared (2-3 days).

To obtain strain D560, the BglII-EcoRI fragment of plasmid 149 (pN3HB derivative containing the mutagenic oligonucleotide between nucleotides 352-353 of the gp63 gene (de Wind et al., J. Virol. 64, 4691–4696 [1990]; numbering according to FIG. 5 of Petrovskis et al., J. Virol. 60, 185–193 [1986]) was replaced by the BglII-EcoRI fragment of plasmid 322 (see FIG. 1). The resulting plasmid, in which the nucleotide sequence between positions 996 of the gp50 gene and 353 of the gp63 gene was replaced by the the sequence TAGGCTAGAATTCTAGCCTA (SEQ ID No 1; the sequence of the mutagenic oligonucleotide) was used together with the overlapping wild-type fragments for the regeneration of virus by means of overlap recombination in G5 cells, as described above.

To obtain strain D1200, plasmid 149 was digested with restriction enzymes BglII and EcoRI, and the resulting larger fragment was treated with the Klenow fragment of E. coli DNA polymerase I to create blunt ends, followed by self-ligation. The resulting plasmid, in which the nucleotide sequence between positions 336 or the gp50 gene and 353 or the gp63 gene was replaced by the sequence AATTCTAGC-CTA (SEQ ID No 2; i.e. remnant of the mutagenic oligonucleotide) was used together with the overlapping wild-type fragments for the regeneration of virus by means of overlap recombination in G5 cells, as described above.

EXAMPLE 3

Replication of gp50 and gp50+gp63 Mutants in Explants of Porcine Nasal Mucosa.

To establish whether these mutants were also able to spread in animal tissue, we used explants of porcine nasal mucosa. These explants offer a natural combination of epithelial cells and stromal fibroblasts, and it has been shown that infection of such explants closely mimics the in vivo infection of nasal mucosa (Pol et al., Res. Vet. Sci. 50, 45–53 [1991]). Explants were infected with the wild-type PRV strain NIA-3, the gp50 linker insertion mutants R122 and R332, and the gp50+gp63 deletion mutants D1200 and D560.

Immunohistochemical examination, at 24 h after infection, using rabbit anti-PRV serum (Pol et el. Res. Vet. Sci. 50, 45–53 [1991]), of infected mucosa explants showed that wild-type virus NIA-3 spread to large areas of the epithelial cells. Similar results were obtained with gp50 mutants R122 and R332, and gp50+gp63 mutants D1200 and D560. After 24 h of infection, virus replication was almost exclusively confined to epithelial cells. However, all strains were able to infect the underlying fibroblasts after longer incubation times. Differential immunological staining by using rabbit anti-PRV serum and monoclonal antibodies (G50N2, specific for gp50) confirmed that gp50 was not expressed by the gp50+gp63 mutants or 81050 mutants. These observations show that gp50 is not essential for virus spread in porcine nasal mucosa.

EXAMPLE 4

Virulence of gp50 and gp50+gp63 Mutants in Mice.

a. gp50+gp63 Null Mutants are lethal for Mice.

The observation that gp50 mutants were able to replicate and spread in tissue explants, suggested that they were also able to replicate and spread in live animals. Mice were chosen as test animals because they are highly susceptible to herpesviruses and have been used extensively as a model system to study virulence and neuronal spread (Fraser and Ramachandran, J. Comp. Path. 79, 435–444 [1969]; Cook and Stevens, Infect. Immun. 7, 272–288 [1973]; Field and Hill, J. Gen. Virol. 23, 145–157 [1974], Field and Hill, J. Gen. Virol. 26, 145–148 [1975]; Kristenson et al., Brain Res. 69, 189–201 [1978]; Platt et al., Arch. Virol. 63, 107–114 [1980]; Dix et al., Infect. Immun. 40, 103–112 [1983]). In the first experiment, we used the gp50+gp63 deletion mutants D560 and D1200, instead of the linker insertion mutants R122 or R332, to exclude the presence of wild-type revertants in the inoculum. Such revertants may arise in stocks of linker insertion mutants by homologous recombination of viral sequences present in the complementing cell line and the virus genome (Cai et al., J. Virol. 62, 2596–2604 [1988]; Peeters et al., J. Virol. 66, 894–905 [1992]; Peeters et al., J. Virol. 66, 3388–3892 [1992]). Since sequences at the 3' side of the gp50+gp63 deletion of strains D560 and D1200 have no homologous counterpart in the complementing G5 cells (FIG. 1), the generation of wild-type revertants should be impossible during replication of these mutants in complementing G5 cells.

Five 6 to 8-week-old female BALB/c mice (Charles River, Suldzfeld, FRG) were infected subcutaneously in the neck with $10^5$ plaque forming units of strains NIA-3, D560, D1200, and the gp63 mutant M105. Mice inoculated with strain NIA-3 developed severe signs of Aujeszky's disease such as vigorous scratching with the hind legs, "face washing" and paralysis, and died at about 70 h after infection. Animals infected with strain M105 did not show extensive pruritus but sat apart with a crooked back and an increased respiration rate. The animals died at about 90 h after infection. Mice infected with strains D560 or D1200 showed symptoms similar to animals infected with strain M105. They became apathetic and showed signs of paralysis before entering a moribund state that sometimes lasted for up to 42 h until the animals died at about 130–140 h after infection (Table 1, experiment 1). These results show that gp50+gp63 null mutants are still lethal for mice. Their virulence, however, is significantly reduced in comparison with the wild-type virus or a gp63 mutant virus.

b. gp50+gp63 Null Mutants are Able to Reach, and Replicate in, the Central Nervous System.

Because symptoms of neurological disorders were much less apparent in mice infected with gp63 or gp50+gp63 mutants in comparison with mice infected with strain NIA-3, the brains of infected animals were examined for the presence of virus by means of immunohistochemistry. Cryostat sections of the brains and organs of infected mice were fixed and processed for immunohistochemistry as described previously (Pol et al, Microb. Path. 7, 361–371 [1989]). When monoclonal antibodies against gp50 were used as primary antibodies, peroxidase conjugated goat anti-mouse immunoglobulin G antibodies were used in the second incubation (Peeters et al., J. Virol. 66, 894–905 [1992]).

To our surprise, we observed that large numbers of infected neurons were present in brain sections of mice infected with D1200 and D560, whereas only small numbers of infected neurons were present in brain sections of mice infected with NIA-3 or M105. The virus that was present in the brains of animals infected with D1200 and D560 did not express gp50, as determined by differential immunostaining using rabbit anti-PRV serum (Pol et al., Res. Vet. Sci. 50, 45–53 [1991]). When virus was isolated from the brains and titrated on SK-6 cells, infectious virus was readily recovered from animals infected with NIA-3 or M105 but not from animals infected with D560 or D1200 (Table 1, experiment 1). These results indicate that gp50+gp63 null mutants that are unable to produce infectious progeny, are still able to reach, and replicate in, the central nervous system.

c. gp50 Null Mutants are Highly Virulent.

Although gp63 is dispensable for viral growth (Petrovskis et al., J. Virol. 60, 1166–1169 [1986]), plaques produced on complementing G5 cells and noncomplementing SK-6 cells by gp50+gp63 mutants were significantly smaller than plaques produced by gp50 mutants. Furthermore, gp63 has been shown to be involved in virulence in pigs (Kimman et al., J. Gen. Virol. 73, 243–251 [1992]). Since these findings suggested that gp50 mutants are more virulent than gp50+gp63 mutants, we also wanted to examine the virulence of gp50 mutants in mice. However, to use a gp50 mutant for the infection of mice, we had to be absolutely sure that the inoculum did not contain wild-type revertants (see above). A batch of phenotypically complemented R122 virus that was virtually free from wildtype revertants was prepared by infecting SK-6 cells with a single plaque produced by R122 on G5 cells. Viral DNA was isolated from the infected SK-6 cells and used to transfect monolayers of 65 cells (which have a greatly reduced plating efficiency for PRV; Peeters et al., J. Virol. 66, 894–905 [1992]). From the transfected cells, a virus batch was prepared that contained $2.1 \times 10^7$ plaque forming units (pfu/ml as determined by titration on SK-6 cells. This batch was designated R122$^+$ to indicate that the virus was phenotypically complemented. A virus batch lacking gp50 was prepared by infecting SK-6 cells with 200 ul ($4.2 \times 10^6$ pfu) of the undiluted R122+ stock. The resulting virus batch, which was designated R122 – to indicate that it was derived from noncomplementing cells, contained 150 pfu/ml. However, when we performed immunoperoxidase staining by using monoclonal antibodies against gp50 (Peeters et el., J. Virol. 66, 894–905 [1992]), these plaques proved to be gp50 negative. This finding indicated that the virus stock did not contain wild-type virus but still contained some infectious virus particles. It is possible that these particles ere derived from the inoculum (R122+) that was used to prepare the R122 – batch. Alternatively, progeny virions may be able to re-incorporate gp50 that was deposited into the plasma membrane of the SK-6 cells by the infecting R122+ virions. Another possibility is that virions lacking gp50 are taken up by endocytosis (Campadelli-Fiume et el., J. Virol. 62, 159–167 [1988]) and occasionally escape degradation, resulting in a productive infection. The physical titre of the R122$^+$ and R122$^-$ stocks was determined with the aid of electron microscopy by using latex beads (diameter 91 nm; Serva) as an internal standard.

In addition to testing the virulence of R122$^+$, we also tested whether virulence of the different viruses was dependent on the route of infection. Groups of five mice were inoculated with $10^5$ pfu of strains NIA-3, M105, R122$^+$ and D1200, by subcutaneous or intraperitoneal injection. Mice that were infected with strain R122$^+$ developed signs of Aujeszky's disease that assembled those seen in NIA-3 infected animals (see above). In animals subcutaneously infected with NIA-3 the first symptoms became apparent at approximately 3–40 h after infection, and in animals subcutaneously infected with R122+ at about 42 h after infection. The animals died at about 56 h and 68 h after infection, respectively (Table 1, experiment 2). These results indicated that gp50 mutant R122$^+$ was still highly virulent for mice and was much more virulent than gp50+gp63 mutant D1200 or gp63 mutant M105. Intraperitoneal injection of strains NIA-3, R122+ and M105, resulted in a mean time to death that was approximately 10–13 h longer competed to subcutaneous injection. For strain D1200 the mean time to death was approximately 25 h shorter after intraperitoneal injection compared to subcutaneous injection (Table 1, experiment 2). For all strains tested, symptoms and clinical signs were independent of the route of infection. Thus, although differences exist in the time course of the infection, both inoculation routes result in a lethal infection. Virus was detected by immunohistochemistry in brain sections of all animals used in experiment 2 (Table 1). Again, virus replication was much more extensive in brains of animals infected with D1200 compared to animals infected with NIA-3, R122+ or M105.

d. Preferential Replication of Virus in Peripheral Nerves of Infected Organs.

When sections of organs were examined for the presence of viral antigens by immunohistochemistry, viral antigens could only be detected in animals that were infected intraperitoneally. Virus was detected in liver, spleen, kidney, intestine and adrenal gland, but not in lungs. Virus infection in organs was almost completely confined to nerve fibers. This observation indicates that nerve tissue is the preferred site of infection and replication of PRV, and suggests that the virus is transported from the organs to the central nervous system by means of retrograde axonal transport, as has been shown previously (Cook and Stevens, Infect. Immun. 7,272–288 [1973]; Field and Hill, J. Gen. Virol. 23, 145–157 [1974], Field and Hill, J. Gen. Virol. 26, 145–148 [1975]; McCracken et al., J. Gen. Virol. 20, 17–28 [1973]; Strack and Loewy, J. Neurosci. 10, 2139–2147 [1990]; Card et el., J. Neurosci. 10, 1974–1994 [1990]). The observation that a gp50 null mutant is efficiently transported to the central nervous system, indicates that neuronal transport is not dependent on the presence of gp50.

Infectious virus was recovered from organ extracts of animals that were infected intraperitoneally with strains NIA-3 and M105. As expected, no infectious virus was recovered from R122+ or D1200 infected animals, again indicating that progeny of these viruses is noninfectious surprisingly, 3 out of 5 animals that were subcutaneously infected with strain NIA-3, yielded infectious virus after titration of organ extracts (Table 1, experiment 2). This could mean that the virus is transported by anterograde movement from the central nervous system to these organs. The absence of infectious virus from organs of mice that were infected subcutaneously with strain M105, probably indicates that transport of this virus was delayed.

e. gp50 is Required for Primary Infection in vivo.

Our in vitro results, which showed that gp50 was required for penetration but not for cell-to-cell spread (Peeters et al., J. Vivol. 66, 894–905 [1992]), suggested that the same was true for infection in vivo.

TABLE 1

Mean time to death and detection of virus in mice infected with different PRV strains.

| | | | | presence of virus | | | |
|---|---|---|---|---|---|---|---|
| | | | mean time to death (h) | (immunohistochemistry) | | (virus isolation) | |
| Exp. virus strain | genotype | route | (+/− S.D.) | brain | organs | brain | organs |
| 1 NIA-3 | wild-type | s.c.[a] | 70.8 +/− 12.9 | + | n.d.[b] | + | n.d. |
| M105 | gp63− | s.c. | 91.2 +/− 18.2 | + | n.d | + | n.d. |
| D560 | gp50-gp63− | s.c. | 132.2 +/− 28.6 | ++ | n.d. | − | n.d. |
| D1200 | gp50-gp63− | s.c | 141.4 +/− 22.4 | ++ | n.d. | − | n.d. |
| 2 NIA-3 | wild-type | s.c. | 55.6 +/− 6.8 | + | − | n.d. | +(3/5) |
| R122+ | gp50− | s.c. | 67.9 +/− 6.8 | + | − | n.d. | − |
| M105 | gp63− | s.c. | 78.6 +/− 18.7 | + | − | n.d. | − |
| D1200 | gp50-gp63− | s.c. | 160.0 +/− 20.4 | ++ | − | n.d. | − |
| NIA-3 | wild-type | i.p.[c] | 67.3 +/− 9.0 | + | +[d] | n.d. | + |
| R122+ | gp50− | i.p. | 77.7 +/− 5.6 | + | +[d] | n.d. | − |
| M105 | gp63− | i.p. | 91.6 +/− 15.6 | + | +[d] | n.d. | + |
| D1200 | gp50-gp63− | i.p. | 134.8 +/− 27.0 | ++ | +[d] | n.d. | − |
| 3 R122+ | gp50− | s.c. | 60.0 +/− 4.2 | + | n.d. | n.d. | n.d. |
| R122− | gp50− | s.c. | 4 × ∞, 1 × 84 | + | n.d. | n.d. | n.d. |
| R145 | gII− | s.c. | ∞ | n.d. | n.d. | n.d. | n.d. |
| R122+ | gp50− | i.p. | 85.2 +/− 5.0 | + | n.d. | n.d. | n.d. |
| R122− | gp50− | i.p. | ∞ | n.d. | n.d. | n.d. | n.d. |
| B145 | gII− | i.p. | ∞ | n.d. | n.d. | n.d. | n.d. |

[a]subcutaneous
[b]not determined
[c]intraperitoneal
[d]in peripheral nerves

Although the possibility that gp50 is not essential for penetration in vivo is highly unlikely, we had to prove formally that in this case also gp50 is required for the primary infection. To examine the involvement of gp50, a batch of R122 was used that was grown on noncomplementing SK-6 cells and thus lacked gp50 (R122−; see above). Because $10^5$ pfu of R122+ corresponded to $3.3 \times 10^6$ physical particles, we used the same number of particles of R122− for the inoculation of mice. As expected, all mice injected intraperitoneally or subcutaneously with R122+ died (Table 1, experiment 3). However, all mice infected with R122− survived after intraperitoneal infection, whereas one out of five animals died after subcutaneous infection. These results indicated that the presence of gp50 in the envelope of the virus was required for successful infection of the animals.

Examination of the animal that died after infection with R122− showed that virus was present in the brain, indicating that infectious virus was still present in the inoculum. When the inoculum was titrated in duplicate on noncomplementing SK-6 cells, we found 9 and 16 plaques, respectively. These plaques were produced by gp50 mutants as determined by immunohistochemistry. The possible origin of these infectious virions has been discussed above. Since the $LD_{50}$ of PRV strain NIA-3, after intraperitoneal infection, is approximately 70 pfu, it is possible that the infectious virus particles present in the R122− inoculum are responsible for the lethal infection of the single animal that died.

f. A Virus that is Unable to Produce Infectious Progeny and that is Unable to Spread by Cell-to-Cell Transmission is Nonvirulent for Mice.

Previously, we have shown that, similar to gp50 null mutants, replication of gII or gH null mutants of PRV in noncomplementing cell lines resulted in the production of noninfectious progeny virions (Peeters et al., J. Virol. 66, 894–905 [1992]; Peters et al., J. Virol. 66, 3388–3892 [1992]). However, in contrast to gp50 mutants, gII and EH mutants were unable to produce plaques on noncomplementing cells. This finding indicated that gII and gH are required for cell-to-cell transmission of the virus. To establish whether cell-to-cell transmission is also a prerequisite for successful virus spread in vivo, we used the phenotypically complemented PRV gII null mutant B145 (Peeters et al., J. Virol. 66, 894–905 [1992]) for the infection of mice. When mice were injected intraperitoneally or subcutaneously with $10^5$ pfu of B145 virus, none of the animals developed any signs of Aujeszky's disease (Table 1 experiment 3). This result indicates that a virus that is unable to produce infectious progeny and that is unable to spread by cell-to-cell transmission is nonvirulent for mice.

EXAMPLE 5

Virulence and Immunogenicity of gp50 Mutants and gp50+gp63 Mutants in Pigs.

To examine the virulence and immunogenicity of the mutant strains, pigs were inoculated with strains R122[30], D560, and D1200. The wild-type strain M209 and the gp63 mutant M102 (FIG. 1) (Kimman et al., J. Gen. Virol. 73,243–251 [1992]) served as controls. Immunization was followed by a challenge with virulent PRV strain NIA-3.

Groups of five 4-to-6 week old pigs (Dutch landrace pigs from the specific pathogen free herd of the Central Veterinary institute) were infected intranasally with $10^5$ pfu of virus by slowly administering 0.5 ml of virus suspension in each nostril during inspiration. Four weeks after vaccination, the pigs were challenged intranasally with $10^5$ pfu of the virulent PRV strain NIA-3. The pigs were observed for clinical signs twice daily and rectal temperatures were taken daily. The animals were weighed three times a week. For each pig, the number of days of growth arrest, fever, and neurological signs were determined. The growth arrest period was defined as the number of days needed to regain the animal's weight on the day of challenge. Fever was defined as a rectal temperature exceeding 40° C. Neurological signs were defined as itching, ataxia, paralysis, tremor and convulsions.

Pigs infected with the wild-type strain M209 developed signs typical of Aujeszky's disease such as fever, loss of appetite, growth retardation and neurological signs such as ataxia and paralysis (Table 2). Mutants R122⁺ and M102 caused short periods of fever and growth retardation but did not evoke neurological signs. Mutants D560 and D1200 did not evoke any neurological signs and did not cause fever or growth retardation. These results indicate that the gp50+ gp63 mutants D560 and D1200 are completely avirulent for pigs, whereas the gp50 mutant R122⁺ and the gp63 mutant M102 have a strongly reduced virulence compared to wild-type PRV.

Pigs vaccinated with strains R122+ and M102 did not show fever or growth retardation and did not develop any clinical signs after NIA-3 challenge inoculation (Table 3). Pigs vaccinated with strains D560 and D1200 showed short periods of fever and growth retardation but did not show neurological signs although the animals were dull for some days and two pigs vomited. Pigs from the unvaccinated control group exhibited severe signs of Aujeszky's disease and relatively long periods of fever and growth retardation; two pigs died (Table 3) These results indicate that pigs vaccinated with the gp50 mutant R122⁺ and the gp63 mutant M102 are completely protected against clinical signs of Aujesky's disease, whereas pigs vaccinated with the gp50+ gp63 mutants D560 and D1200 are partially protected against clinical signs of Aujeszky's disease.

TABLE 2

Immunization of pigs with different PRV strains$

| Immunization | fever* | growth retardation* | clinical signs |
|---|---|---|---|
| M209 (n = 3) | 5.3 +/– 0.6 | 8.3 +/– 7.3 | ++ |
| M102 (n = 4)# | 2.4 +/– 1.5 | 2.4 +/– 2.2 | – |
| R122⁺ (n = 5) | 3.8 +/– 1.6 | 0.8 +/– 1.8 | – |
| D560 (n = 5) | 0 | 0 | – |
| D1200 (n = 5) | 0 | 0 | – |

$no pig died during the experiment
*mean number of days (+/– S.D.)
One pig died, probably as a result of trauma after collecting blood samples.
++ denotes neurological signs such as ataxia, convulsions and paralysis

TABLE 3

Protection of vaccinated pigs after challenge with NIA-3

| Immunization | Mortality | fever* | growth retard.* | clinic. signs |
|---|---|---|---|---|
| — (n = 6) | 2 | 6.8 +/– 0.5 | 10.3 +/– 7.1 | ++ |
| M102 (n = 4) | 0 | 0 | 0 | – |
| R122⁺ (n = 5) | 0 | 0 | 0 | – |
| D560 (n = 5) | 0 | 2.6 +/– 1.3 | 4.6 +/– 6.5 | +/– |
| D1200 (n = 5) | 0 | 3.6 +/– 1.1 | 1.4 +/– 3.1 | +/– |

*mean number of days (+/– S.D.)
++ denotes neurological signs such as ataxia, convulsions and paralysis
+/– denotes dullness (sometimes vomiting, see text)

These examples show that gp50 of PRV is essential for infectivity of the virus (penetration) but not for cell-to-cell transmission. Phenotypically complemented gp50 mutants and gp50+gp63 mutants are able to replicate and spread in infected animals. However, progeny virus released from infected cells is noninfectious and thus infected animals are unable to shed infectious virus. This property, together with the broad host range of PRV and the ability to accomodate large amounts of foreign DNA makes PHV gp50 mutants ideally suited for the preparation of safe (carrier) vaccines against Aujeszky's disease and other animal diseases.

EXAMPLE 6

Construction of a gp50 Deletion Mutant that Expresses Envelope Glycoprotein E1 of Hog Cholera Virus.

To test whether a gp50 deletion mutant can be used as a vector virus for the expression of heterologous genes, the gp50 gent of PRV strain NIA-3 was replaced by a DNA fragment containing the E1 gene of Hog Cholera Virus (HChV=classical swine fever) under the transcriptional control of the hCMV promoter.

A ScaI-DraI fragment (ScaI site at position 317–322 of gX gene, nucleotide sequence numbering of Rea et al., J. Virol. 54, 21–29 [1985]; DraI site at position 1181–1186 between gp63 and gI gene, nucleotide sequence numbering of Petrovskis et al., J. Virol. 60, 185–193 [1986]) from the U.S. region of PRV was cloned in the blunted NdeI site of plasmid pUC19M (Clontech). By means of site-specific in vitro mutagenesis (Transformer kit, Clontech) unique restriction enzyme recognition sites were created just in front of the gp50 gene and just behind the gp50 gene. By using the mutagenic primers 5'-AGGTrCCCATACACTAGTCCGCCAGCGCCA-TGC-3' (SEQ ID NO: 3) and 5'-CCCGGTCCGTAGCCTAGGCAGTACCGGCGTCG-' (SEQ ID N0: 4), recognition sequences for the restriction enzymes SpeI (ACTAGT) and AvrII (CCTAGG) were created at positions −17 to −12 and 1210 to 1215, respectively (nucleotide sequence numbering of gp50 gene according to Petrovskis et al., J. Virol. 59, 216–223 [1986]). The gp50 gene was deleted by digestion of the plasmid DNA with SpeI and AvrII and was replaced by a synthetic SpeI-AvrII DNA fragment that contained recognition sequences for the restriction enzymes EcoRI, EcoRV and HindIII (the synthetic DNA fragment was obtained by annealing equimolar amounts of two single-stranded oligonucleotides with sequence 5'-CTAGTGAATTCGATATCAAGC-TTC3' (SEQ ID NO: 5) and 5' CTAGGAAGCTTGATATCGAATTCA-3' (SEQ ID NO: 6), respectively). Subsequently, a NcoI-PstI fragment (NcoI site at position 883–088 of gX gene, nucleotide sequence numbering of Rea et al., J. Virol. 54, 21–29 [1985]; PstI site at position 439–444 of gp63 gene, nucleotide sequence numbering of Petrovskis et al., J. Virol. 60, 185–193 [1986]) containing the gp50 deletion was cloned in plasmid pGEM5Zf(+) (Promega) after digestion of the latter plasmid with NcoI and PstI. The resulting plasmid was designated pBp53.

Figure 2:
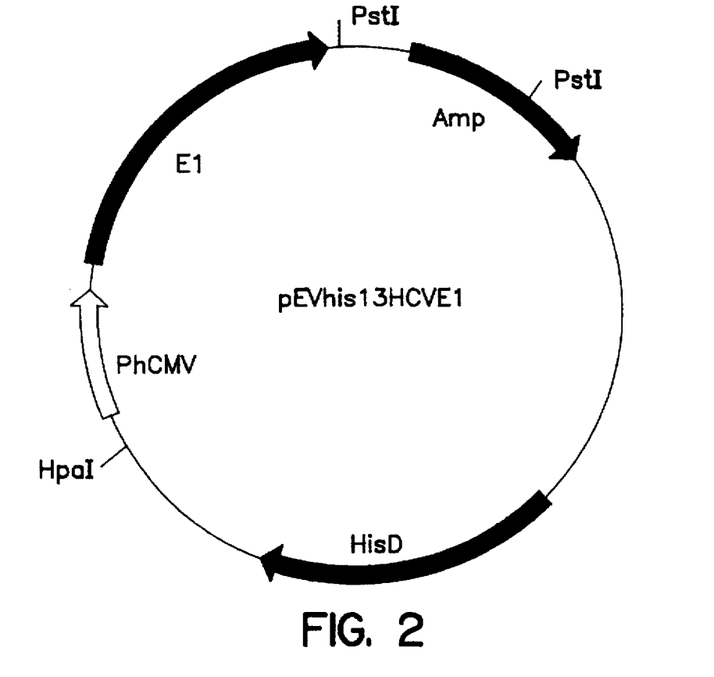
Figure 3:
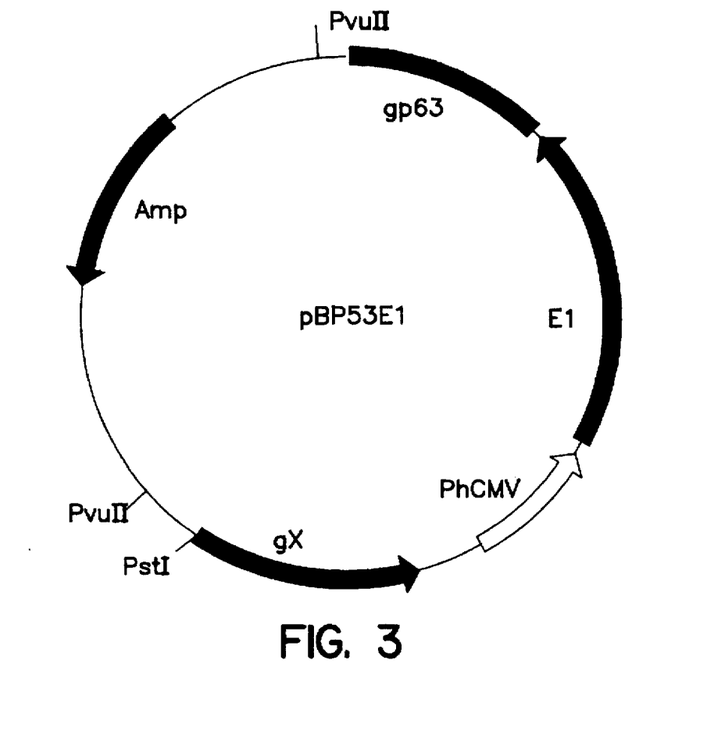

The E1 gene of HChV was derived from a cDNA clone of HChV strain Brescia (Moormann et al., Virology 177, 184–198 [1990]). The gene was cloned as a DsaI-EcoRV fragment (DsaI site filled in with the Klenow fragment of E.coli DNA Polymerase I; nucleotides 2337–3804 according to nucleotide sequence numbering of Noormann et al., Virology 177, 184–198 [1990]) between the EcoR1 site (filled in with the Klenow fragment of E.coli DNA polymerase I) and the EcoRV-site of plasmid pEVhisl3. The latter plasmid is a derivative of plasmid pSV2his (Hartman and Mulligan. Proc. Natl. Acad. Sci. USA 85, 8047–8051 [1988]) which contains the hCMV promoter followed by an AT& start codon, a number of unique restriction sites and translational stopcodons in all three reading frames (Peeters et al., J. Virol. 66, 894–905 [1992]; also see example 1). In the resulting plasmid the E1 gene is fused in-frame with the startcodon of pEVhis13. This plasmid was designated pEVhis13HCVE1 (FIG. 2). After digestion of plasmid pEVhis13HCVE1 with HpaI and PstI, a fragment was isolated that contained the hCMV promoter, the E1 gene, and the translational stopcodons. The HpaI-PstI fragment was treated with T4 DNA polymerase to create blunt ends and was subsequently cloned in the EcoRV site of pBp53. A plasmid in which the fragment was inserted in such an orientation that the direction of transcription of the E1 gene was similar to that of the gX and gp63 genes of pBp53 was isolated and was designated pBp53E1 (FIG. 3).

To test whether the E1 gene had been correctly cloned, transient expression of E1 was examined in G5 cells. Cells were transfected with plasmid pBp53E1 or pEVhis13HCVE1 by using lipofectin (GIBCO BRL). After 2 days the monolayers were fixed and expression of E1 was tested by immunological staining by using horseradish peroxidase-conjugated monoclonal antibodies 3 and 4 specific to glycoprotein E1 of HChV (Wensvoort, J. Gen. Virol.70 2685–2876 [1989]). Expression of E1 by cells that had been transfected with pBp53E1 was clearly visible and the staining was even more intense than that of cells transfected with pEVhis13HCVE1. These results indicated that E1 is efficiently expressed in the context of pBp53E1, i.e., when bordered by PRV sequences.

Plasmid PBP53E1 was digested with PvuII and PstI and cotransfected, together with viral DNA of PRV strain NIA-3, in G5 cells by using lipofectin. After 2 days, when plaques were clearly visible, the monolayers were fixed and immunologically stained as described above for the transient expression assay. The presence of stained plaques indicated that the E1 gene had been transferred to the viral genome by means of homologous recombination, and that the E1 gene was expressed by recombinant viruses. To isolate a recombinant virus, the transfection experiment was repeated and 400 individual plaques were isolated. To identify recombinants that expressed E1, part of the isolates was transferred to microtiter plates containing SK-6 cells. After incubation for 2 days, plaques were visible and the infected monolayers were fixed and tested for the expression of E1 by immunological staining. Finally, recombinant virus that expressed E1 was plaque purified from original isolates that yielded stained plaques on SK-6 cells.

It has been shown that a recombinant vaccine strain of PRV that expresses E1 of HChV protects pigs from classical swine fever after challenge-inoculation with HChV (van Zijl et al., J. Virol. 65, 2761–2765 [1991]). Based on these findings, the non-transmissible E1-expressing gp50 deletion mutant described above will also be able to induce a protective immune response against classical swine fever in pigs.

We claim:

1. A vaccine comprising a pseudorabies virus containing glycoprotein gp50 and having a mutation in its gp50 gene, together with a pharmaceutically acceptable carrier or diluent.

2. A vaccine according to claim 1 wherein the mutation is a deletion.

3. A vaccine according to claim 1 wherein the mutation is an insertion comprising a heterologous gene encoding an antigen corresponding to an animal disease other than Aujesky's disease.

4. A vaccine according to any of claim 1, wherein the pseudorabies virus additionally has at least one mutation in one of its other genes.

5. A vaccine according to claim 4, wherein said at least one additional mutation is in the gp63 gene.

6. A vaccine according to claim 4, wherein said at least one additional mutation is in the gI gene.

7. The vaccine according to claim 1, wherein said mutated pseudorabies virus contains an additional mutation at a site other than the gp50 gene, and wherein said additional mutation is an insertion of a heterologous gene that encodes an antigen of an animal pathogen.

8. A method for preventing and/or controlling an animal disease, comprising administering an immunogenically effective amount of the vaccine according to claim 1.

9. The method for preventing and/or controlling an animal disease, which comprises administering an immunogenically effective amount of a vaccine according to claim 2.

10. The method for preventing and/or controlling an animal disease, which comprises administering an immunogenically effective amount of a vaccine according to claim 3.

* * * * *